United States Patent [19]
Westermann et al.

[11] Patent Number: 5,908,944
[45] Date of Patent: Jun. 1, 1999

[54] METHYLATION OR ETHYLATION AGENT AND PROCESS FOR 1,4-ADDITION OF A METHYL OR ETHYL GROUP TO AN α, β-UNSATURATED KETO COMPOUND

[75] Inventors: Jürgen Westermann; Klaus Nickisch, both of Berlin, Germany

[73] Assignee: Schering Aktiengesellschaft, Germany

[21] Appl. No.: 08/211,230

[22] PCT Filed: Sep. 28, 1992

[86] PCT No.: PCT/EP92/02227

§ 371 Date: Sep. 30, 1994

§ 102(e) Date: Sep. 30, 1994

[87] PCT Pub. No.: WO93/06066

PCT Pub. Date: Apr. 1, 1993

[30] Foreign Application Priority Data

Sep. 27, 1991 [DE] Germany ............................. 41 32 755

[51] Int. Cl.$^6$ ................. C07J 1/00; C07J 7/00; C09K 3/00; C07D 317/72
[52] U.S. Cl. ............ 552/634; 552/604; 552/641; 552/643; 549/336; 252/183.13; 568/329; 568/330; 568/376
[58] Field of Search .............. 252/183.13; 552/634, 552/641, 643, 604; 549/336; 568/376, 330, 329

[56] References Cited

U.S. PATENT DOCUMENTS

| | | | |
|---|---|---|---|
| 4,404,344 | 9/1983 | Sinn et al. ............................. | 526/160 |
| 5,043,515 | 8/1991 | Slaugh et al. .......................... | 585/512 |

FOREIGN PATENT DOCUMENTS

| | | | |
|---|---|---|---|
| 48030789 | 4/1973 | Japan . | |

OTHER PUBLICATIONS

Kuchin et al., Highly Selective Carboalumination of mono-substituted acetylenes by alumino cuprate reagents, Izv. Akad. Nauk SSSR, Ser. Khim, 1987, 2, 397–403, 1987.

Bagnell et al., "Nickel Catalysed Conjugate Addition of Trimethylaluminium to alpha, beta–Unsaturated Ketones", *Australian Journal of Chemistry*, vol. 28 (1975), pp. 801–815.

Bagnell et al., "Nickel Catalyzed Conjugate Addition of Trymethylaluminium to 3–oxo–delta4–steroids", *Australian Journal of Chemistry*, vol. 28 (1975), pp. 817–820.

Merck Index, Ninth Edition, (1976) pp. 769, 5762.

Ashby, et al. *J. of Org. Chem.*, 39, pp. 3297–3299, 1974.

*Primary Examiner*—José G. Dees
*Assistant Examiner*—Alton Pryor
*Attorney, Agent, or Firm*—Millen, White, Zelano, & Branigan, P.C.

[57] ABSTRACT

This invention describes a new methylation or ethylation agent containing trimethyl aluminum or dimethyl zinc or triethyl aluminum as methyl or ethyl source, which additionally contains catalytic amounts of one or more copper(I) and/or copper(II) compounds as well as a process for the 1,4-addition of a methyl or ethyl group to an α,β-unsaturated or an α,β-double unsaturated ketone or an α,β-unsaturated aldehyde using the agent according to the invention.

By using only catalytic amounts of copper and a CKW (chlorinatedhydrocarbon)-free reaction medium, the new methylation/ethylation agent/process is distinguished by its environmental compatibility and it is, for example, suitable for the production of initial products for the synthesis of biologically effective compounds.

21 Claims, No Drawings

METHYLATION OR ETHYLATION AGENT AND PROCESS FOR 1,4-ADDITION OF A METHYL OR ETHYL GROUP TO AN α, β-UNSATURATED KETO COMPOUND

This application is a 371 of PCT/EP92/02227 filed Sep. 28, 1992.

This invention relates to a methylation or ethylation agent and a process for the 1,4-addition of a methyl or ethyl group to an α,β-unsaturated or an α,β-double unsaturated ketone or an α,β-unsaturated aldehyde.

The 1-methyl introduction in steroids is a first and an important synthesis step in the production of 1-methyl steroids. Examples of this class of substances are atamestan (1) (1-methylandrosta-1,4-diene-3,17-dione), an inhibitor of estrogen biosynthesis (aromatase inhibitor) and mesterolone (2) (1α-methylandrosta-17β-ol-3-one), a steroid with androgenic effect.

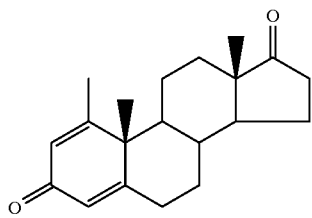

Atamestan (1)

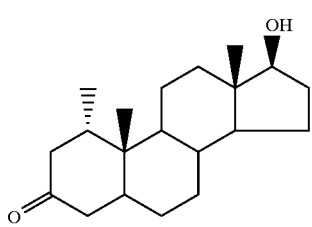

Mesterolon (2)

A known method for the introduction of 1-methyl in, e.g., (3) (androsta-1,4-diene-3,17-dione) to (4) (1-methylandrost-4-ene-3,17-dione) is the addition of dimethyl copper-lithium which is produced from methyl lithium and copper(I)-halides. Molar amounts of the corresponding copper salt are necessary for this purpose. A marked excess of reagent Me₂CuLi is necessary to achieve a complete conversion in the reaction to 4.

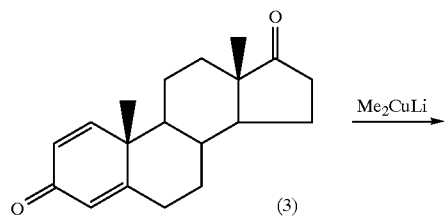

Androsta-1,4-dien-3,17-dion (3)

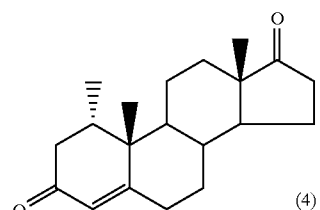

1α-Methyl-androst-4-en-3,17-dion (4)

This process is an object of German patents 204 66 40 and 225 30 87. The copper salts thus accumulating in molar amount, that have to be worked up, represent a great problem, however they are extremely difficult to separate by filtration.

The accumulation of sizable amounts of copper salts can be avoided by copper(I)-catalyzed 1,4-addition with methyl magnesium halides, but an undesirable 1,2-addition as secondary reaction occurs in this way. Thus, under these conditions, androsta-1,4-diene-3,17-dione (3) cannot be methylated to the desired product 1α-methyl-androst-4-ene-3,17-dione (4). Rather 3-exomethyleneandrosta-1,4-dien-17-one (5) is formed here by attack on the 3-carbonyl group and after elimination of water from the intermediarly formed carbinol.

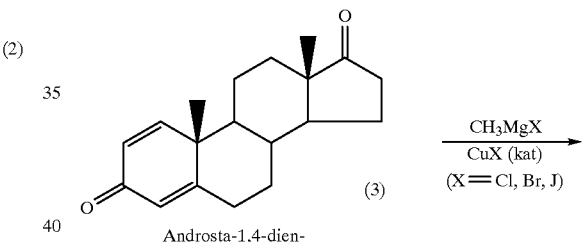

Androsta-1,4-dien-3,17-dion (3)

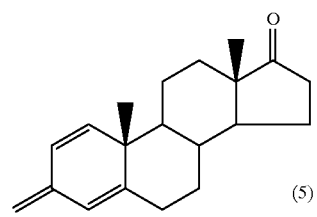

3-Exomethylen-androsta-1,4-dien-17-on (5)

There are only few examples in the literature of a 1,4-addition to an α,β-double unsaturated carbonyl system, as is the case in the example of androsta-1,4-diene-3,17-dione (3). To go directly from 3 to 4, as explained above, molar amounts of dimethyl copper lithium are always necessary, that must be produced from molar amounts of methyl lithium and copper(I) halides.

The reaction sequence of M. Tanabe and D. F. Crowe in Can. J. Chem. 45, 475 (1967) shown in the following diagram and in German patent 1 223 837 is described as another method for the introduction of a methyl group in a steroid in 1-position under catalytic conditions.

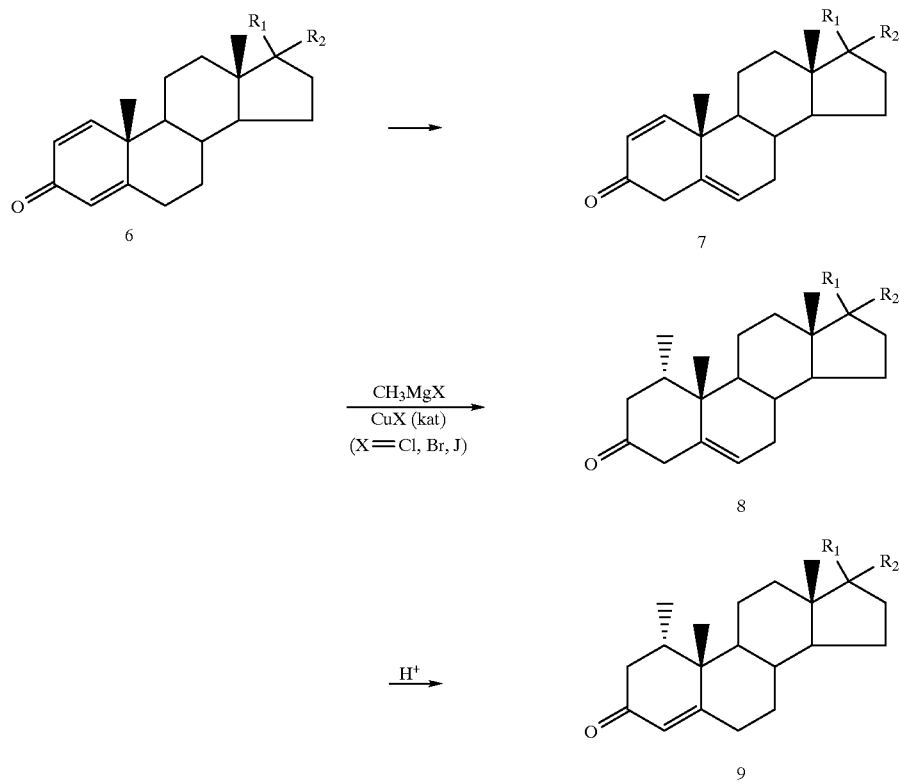

For this purpose a conversion of the 1,4-diene system 6 into a 1,5-diene steroid compound 7 is first necessary.

The subsequent addition to the deconjugated 1,5-diene system 7 is possible under catalytic conditions, although in practice the yields in the decisive addition step 7 to 8 do not exceed 50%. Because of the additional number of stages and, connected therewith, reduced total yield, all things considered no advantageous and economical process is available with the above-described multistage sequence.

Thus so far neither a usable transition-metal catalytic process nor a suitable methylation agent is available for the introduction of a methyl group in 1-position in a 3-keto-1,4-diene steroid (1,4-addition), for example, androsta-1,4-diene,3,17-dione (3).

The object of this invention is to make available a new methylation or ethylation agent as well as to indicate a new transition-metal catalytic process for the 1,4-addition of a methyl or ethyl group to an α,β-unsaturated or an α,β-double unsaturated ketone or an α,β-unsaturated aldehyde using this new alkylation agent indicated. The process to be developed is to be suitable especially for the 1-methylation of 3-keto-1,4-diene steroids.

This object is achieved by the alkylation agent according to the invention, which contains trimethyl aluminum or dimethyl zinc or triethyl aluminum as methyl or ethyl source as well as in addition catalytic amounts of one or more copper(I) and/or copper(II) compounds.

Preferably the alkylation agent altogether contains 5–10 mol % of copper(I) and/or copper(II) compound relative to the α,β-unsaturated keto compound to be alkylated.

As copper(I) and/or copper(II) compound(s), first of all, one or more compound(s) of general formula I $$\text{CuX oder CuX}_2 \qquad (I)$$

or are suitable in which X represents a monovalent radical and stands for chlorine, bromine, iodine, cyano, the thienyl, phenyl, an alkoxy, thioalkoxy, and the alkyl radical contained in it has 1 to 8 carbon atoms and is optionally branched and/or unsaturated, stands for a substituted alkinyl radical R—C≡C— and R means a phenyl or an optionally branched $C_1$–$C_8$-alkyl radical, or stands for the radical of an inorganic acid or a carboxylic acid or for a bidentate complex ligand that is coordinated by oxygen and/or nitrogen atoms, excluding the ligand acetylacetonate in the case of the divalent copper, and/or one or more compound(s) of general formula II $$\text{Cu}_2\text{Y oder CuY} \qquad (II),$$

or in which Y represents a divalent radical and stands for oxygen or sulfur. If X is the radical of an inorganic acid, for example, the bicarbonate radical, the hydrogen sulfate radical or similar radicals are meant. Above all, the acetate radical is suitable as radical of an organic acid.

Especially copper(I) and/or copper(II) chloride or bromide as well as copper(I) cyanide is meant as transition-metal catalyst.

Moreover, the alkylation agent according to the invention additionally can contain up to 1 mol % in nickel salt(s); in this way an acceleration of the methylation can be achieved under certain conditions. For example, nickel-II-acetylacetonate, nickel-bis-triphenylphosphane-dichloride, nickel dichloride or a similar compound can be used as nickel salt.

Aluminum trimethyl and aluminum triethyl as well as zinc dimethyl can be used as toluene or hexane solution. Because of the problematic handling and self-ignitability of the metal alkyls, their use in solution as opposed to the use in pure form is preferred.

Only to a small extent do aluminum-organic compounds enter into a 1,2-addition under normal reaction conditions without addition of a catalyst. It is known in the literature that such a reaction occurs only under drastic reaction conditions (higher temperatures). Under normal conditions such a reaction only occurs when a second trimethyl aluminum molecule is available. The first trimethyl aluminum molecule complexes the carbonyl group, then the second molecule is added to the thus activated carbonyl group (E. C. Ashby et al., J. Am. Chem. Soc., 90 (1968) 5179). A survey of aluminum alkyls is found in T. Mole and E. A. Jeffry in "Organoaluminum Compounds", Elsevier 1972, page 294 ff.

1,4-additions with Me$_2$AlJ are possible, but they take place in competition with 1,2-addition and without addition of copper as catalyst (J. Ashley et al., J. Org. Chem., 44 (1979) and are not selective.

In the process according to the invention for the 1,4-addition of a methyl or ethyl group to an α,β-unsaturated keto compound, this α,β-unsaturated keto compound is alkylated with aluminum trimethyl or zinc dimethyl or aluminum triethyl in the presence of a catalytic amount or one or more copper(I) and/or copper(II) compounds. The desired 1,4-addition runs smoothly. Further configurations of the process according to the invention follow from the features of subclaims 10–21.

There are still no examples in the literature for such a catalytic processing method.

The test of the methylation of isophorone (3,5,5-trimethyl-2-cyclohexen-1-one) with trimethyl aluminum in the presence of 6.6 mol % of copper(II) acetylacetonate (relative to isophorone) described in Aust. J. Chem., 1975, 28, pp 801–815 was unsuccessful. That copper(II) acetyl actonate is unsuitable as methylation catalyst, is confirmed by the reaction tests described in examples 18 and 19.

In the process according to the invention a copper(I) compound is converted into a methyl copper or dimethyl copper compound, that, as such, brings about the 1,4-addition. After transfer of a methyl group to the substrate (enone) the reactive and 1,4-selective copper reagent can be formed again in a cyclic process from trimethyl aluminum.

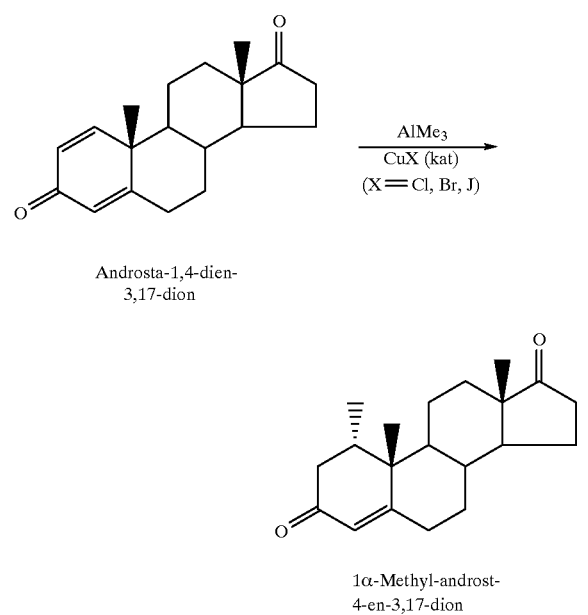

Androsta-1,4-dien-3,17-dion

1α-Methyl-androst-4-en-3,17-dion

Chloride or bromide is preferably used as copper(I) halide. The reaction is preferably performed in tetrahydrofuran, dioxane, dimethoxyethane, toluene or else in ethyl acetate as solvent. Surprising in this connection is that no reaction with the carboxylic acid ester group of the ethyl acetate takes place under the found reaction conditions. An advantage of ethyl acetate as solvent lies in the environmental compatibility of this solvent that consists of the naturally occurring groups acetic acid and ethanol and can be hydrolyzed or catabolized in the environment in these natural molecules.

In addition to copper(I) halides, copper(II) halides, copper (II) compounds such as CuO and CuS are also suitable for the reaction. Copper(II) complexes, in which the copper is coordinated with ligands, have also proven well suited.

Such complexes of formulas 10 and 11 are described in the literature by L. Sacconi et al. in J. Chem. Soc., 1964, 276, that are derived from salicylaldehyde and are able to be produced from it.

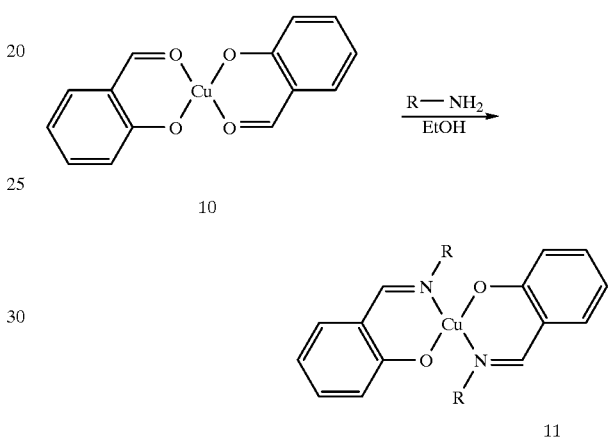

Addition of salicylaldehyde to a copper(II) salt solution after filtration yields complex 10 that after isolation and reaction with an amine, such as, e.g., isopropylamine, yields the Schiff base in complex 11. Other complexes can be produced analogously. When using copper(II) compounds as catalysts copper(I) compounds—resulting by reduction—probably also represent the active species.

In all of these copper(I) and copper(II) compounds the use of catalytic portions is sufficient. In this case, preferably an amount of 5–10 mol % of copper compound is used relative to the enone used.

The high 1-selectivity of this addition is worth mentioning in addition to the pronounced 1,4-selectivity in the addition to a 1,4-diene-3-keto steroid. Preferably an addition in 1-position of the steroid to 4 takes place that is markedly preferred relative to the sterically more strongly shielded 5-position.

The new process is highly stereoselective; the part of the 5β-methyl compound formed as by-product, (in the case of methylation of (3) 5β-methyl-androst-1-ene-3,17-dione) is under 5% in the crude product.

Another advantage of the described process is that acetyl protective groups remain intact under the reaction conditions. As described in example 6, for example, the conversion of 17β-acetoxy-androst-1-en-3-one into 17β-acetoxy-1α-methyl-5α-androstan-3-one with a yield of 89% or 95% is possible.

The isolation of the products preferably takes place by crystallization of the reaction products or by chromatography. The yields in product are up to 99% of theory.

Substance 1α-methylandrost-4-ene-3,17-dione (4) available according to the described catalytic process from ADD (3) is an important intermediate stage for the synthesis of mesterolone (2).

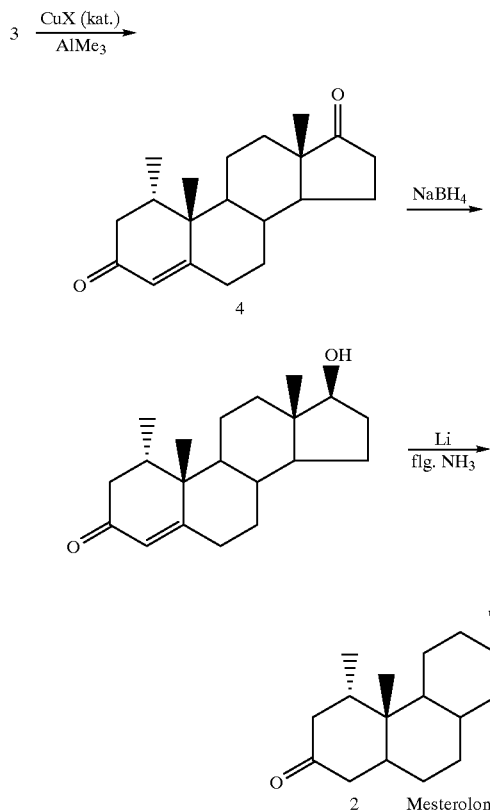

Literature: DE-1 152 100 B; DE-2 046 640 B; NaBH₄ reduction: Fried & Edwards, Organic Reactions in Steroid Chemistry, Vol I, 1972, p 61 ff, Van Nostrand Reinhold Company, New York; Birch-Reduction: Fried & Edwards, Vol. I, p. 39.

17β-Acetoxy-1α-methyl-5α-androstan-3-one (example 6) is also suitable as initial product for the production of mesterolone, which can be obtained easily from the former by saponification of the 17β-acyl group.

If a carboxylic acid anhydride or chloride is added to the reaction solution before the working up of reaction 3→4, then the enolate present in the reaction can be trapped as enol ester e.g., 13.

As carboxylic acid anhydride or chloride, the anhydrides of straight or branched chain alkane carboxylic acids with 2 to 8 carbon atoms, especially acetic acid as well as benzoic acid, are suitable.

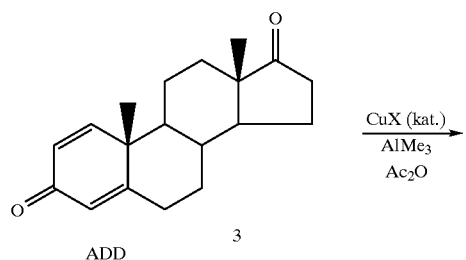

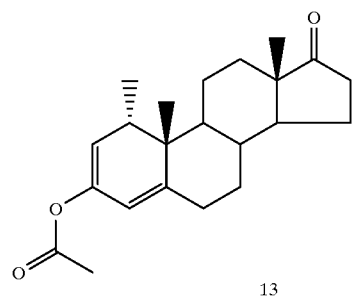

3-Acetoxy-1α-methyl-androsta-2,4-dien-17-one (13) is an important intermediate product for the synthesis of atamestan, which is obtained in a high yield from it by stereoselective 2β-iodization as well as subsequent iodine dehydrogenation (German patent application P 40 15 247.2 and DE-A-37 15 869.4). This representation of atamestan is known from example 20.

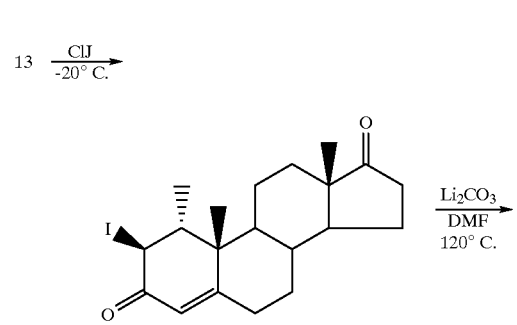

The process according to the invention is also suitable to enter into a 1,4-addition in a singly, unsaturated carbonyl system such as, e.g., 14.

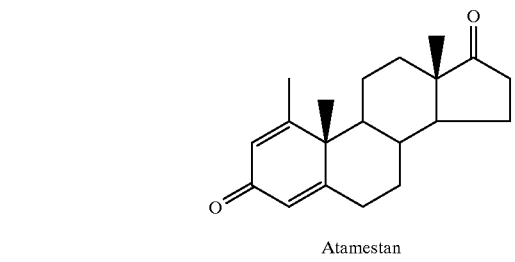

Androst-4-en-3,17-dion (14)

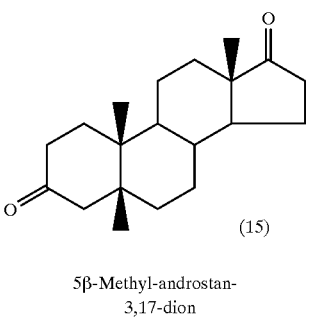

5β-Methyl-androstan-3,17-dion

Thus 5β-methyl-androstane-3,17-dione (15) results from androst-4-ene-3,17-dione (14).

Beyond the above-indicated 1,4-addition in α,β-unsaturated keto steroids the process according to the invention is applicable quite generally for the 1,4-addition of a methyl or ethyl group to an α,β-unsaturated ketone. An example of this is the reaction of cyclohex-2-en-1-one (16) to 3-methylhexanone (17).

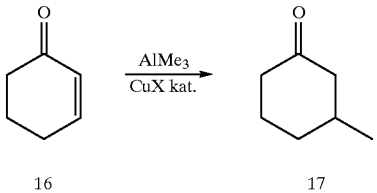

16　　　　　　　17

All reactions are preferably performed between 0° C. and 50° C. For the reaction the ketone or keto steroid is introduced in a suitable solvent with addition of 5–10 mol % of copper catalyst under an atmosphere of inert gas such as, e.g., nitrogen and aluminum trimethyl (zinc dimethyl, aluminum triethyl) is added between 0° C. and room temperature. The reaction is hydrolyzed after approximately 30–120 minutes with addition of water or a lower alcohol and the product is then isolated.

The agent according to the invention and the described process are not limited to the use of trimethyl aluminum or dimethyl zinc or triethyl aluminum as methyl or ethyl source. It has been found that quite analogously to the above-described instead of the mentioned alkylation reagents also an aluminum reagent of formula $Alk_{3-n}$-$AlOEt_n$, in which Alk means a methyl or ethyl group and OEt means an ethoxy group and n equals 1 or 2, can be used as the methyl or ethyl group providing reagent within the agent or process according to the invention. If Alk stands for a methyl group, then n preferably is 1 (dimethyl aluminum-ethoxide).

The examples described below are to show the breadth of the process according to the invention. The yields achieved in this way are to show the advantage of the new catalytic process for 1-methyl or ethyl introduction in steroids and demonstrate the general possibility for the 1,4-addition to enone systems and dienone systems.

EXAMPLE 1

1α-Methylandrost-4-ene-3, 17-dione 14.2 g (50 mmol) of androsta-1,4-diene-3,17-dione is dissolved under nitrogen atmosphere in 100 ml of anhydrous dioxane. 716 mg (5 mmol) of copper(I) bromide is added and the solution is heated to 25° C. Then 47 ml (55 mmol) of a 10% solution of trimethyl aluminum in toluene is added to the reaction so that the temperature does not rise above 35° C. Then it is stirred for 1.5 hours more at 35° C. For the hydrolysis, 2.5 ml of water mixed with 10 ml of dioxane is added to the reaction and the solution is stirred for 15 minutes more. The inorganic solid is suctioned off and washed again with 30 ml of dioxane. After concentration by evaporation of the dioxane solution, 17 g of crude product is obtained, that is chromatographed on silica gel with an hexane/ethyl acetate mixtures as eluent. After concentration by evaporation of the fractions and recrystallization from diisopropyl ether, 11.66 g of 1α-methylandrost-4-ene-3,17-dione (77% of theory) of a melting point of 154° C. is obtained.

EXAMPLE 2

5β-Methyl-19-norandrostane-3,17-dione 2.72 g (10 mmol) of 19-norandrost-4-ene-3,17-dione is dissolved in 20 ml of dioxane at 20° C. and mixed with 143.3 g (1 mmol) of copper(I) bromide. 9.4 ml (11 mmol) of a 10% solution of trimethyl aluminum in toluene is added to the reaction at 30° C. under nitrogen atmosphere and stirred for 30 minutes at 30–40° C. For hydrolysis, 0.54 ml of water dissolved in 5 ml of dioxane is added to the reaction. It is stirred for 10 minutes more and the precipitate is filtered off. The precipitate is washed again with a little dioxane. The dioxane solution is concentrated by evaporation on a rotary evaporator and the residue is chromatographed on silica gel with ethyl acetate/hexane as eluent. After concentration by evaporation of the fractions, 2.6 g of 5β-methyl-19-norandrostane-3,17-dione (90% of theory) of a melting point of 155.9° C. is obtained.

EXAMPLE 3

1α-Methyl-17β-acetoxy-androst-4-en-3-one 3.28 g (10 mmol) of 17β-acetoxy-androsta-1,4-dien-3-one is dissolved in 20 ml of dried dioxane and mixed with 143.3 mg (1 mmol) of copper(I) bromide. 9.4 ml of a 10% solution of trimethyl aluminum in toluene is added for 10 minutes to the reaction under nitrogen atmosphere so that the temperature does not rise above 40° C. Then it is stirred for 2 hours more at 40° C. For hydrolysis, 0.54 ml of water dissolved in 5 ml of dioxane is added to the reaction and stirred for 10 minutes more. The solid is suctioned off on diatomaceous earth and washed again with 20 ml of dioxane. The filtrate is concentrated by evaporation and the crude product (3.6 g) is chromatographed on silica gel with hexane/ethyl acetate mixtures as eluent. After concentration by evaporation of the fractions, 2.6 g of 1α-methyl-17β-acetoxy-androst-4-en-3-one (75.58% of theory) of a melting point of 142° C. is obtained.

EXAMPLE 4

5β-Methylandrostane-3,17-dione 2.86 g (10 mmol) of androst-4-ene-3,17-dione and 143.3 mg (1 mmol) of copper(I) bromide are dissolved in 20 ml of dry dioxane. 9.4 ml (11 mmol) of a 10% solution of trimethyl aluminum in toluene is added to the reaction for 10 minutes at room temperature under nitrogen atmosphere so that the temperature does not rise above 30° C. Then it is stirred for 2 hours more at 30° C. For hydrolysis, 0.54 ml of water dissolved in 5 ml of dioxane is added to the reaction and stirred for 10 minutes more. The solid is suctioned off on diatomaceous earth and washed again with 20 ml of dioxane. The filtrate is concentrated by evaporation and the crude product (3.0 g) is chromatographed on silica gel with hexane/ethyl acetate as eluent and an increasing part of ethyl acetate. After concentration by evaporation of the fractions, 2.3 g of 5β-methyl-androsta-3,17-dione (76% of theory) of a melting point of 135° C. is obtained.

EXAMPLE 5

17β-Hydroxy-1α-methyl-androst-4-en-3-one (1α-methyl-testosterone)

2.84 g (10 mmol) of androsta-1,4-diene-3,17-dione is dissolved in 20 ml of anhydrous dioxane under nitrogen atmosphere. 143.3 mg (1 mmol) of copper(I) bromide is added and the solution is heated to 25° C. Then 9.4 ml (11 mmol) of a 10% solution of trimethyl aluminum in toluene is added to the reaction so that the temperature does not rise above 35° C. Then it is stirred for 1.5 hours more at 35° C. For hydrolysis, 0.54 ml of water mixed with 5 ml of dioxane is carefully added to the reaction and the solution is stirred for 15 minutes more. The inorganic solid is suctioned off and washed again with 30 ml of dioxane. After concentration by evaporation of the solution, 3.1 g of 1α-methylandrost-4-ene-3,17-dione is obtained, that is dissolved in 8 ml of methanol and cooled to −5° C. internal. temperature. 0.18 g of sodium borohydride is added to 0.5 ml of water cooled to 5° C. and the sodium borohydride-water solution is added to the solution of 1α-methyl-androst-4-ene-3,17-dione so that the temperature does not rise above −5° C. Then it is stirred for 40 minutes more at −5° C. After DC check to determine whether the reaction has occurred, 0.33 ml of acetic acid in 1 ml of water is carefully added until no more gas generation is detectable. The solution is taken up in 50 ml of ethyl acetate and washed twice with 20 ml of water each. The organic phase is dried with sodium sulfate. After concentration by evaporation of the solution and recrystallization from acetone, 2.29 g of 17β-hydroxy-1α-methyl-androst-4-en-3-one (75% of theory) of a melting point of 195° C. is obtained.

EXAMPLE 6

17β-Acetoxy-1α-methyl-5α-androstan-3-one

Variant 1 (in dioxane): 3.30 g (10 mmol) of 17β-acetoxy-androst-1-en-3-one is dissolved in 20 ml of dried dioxane and mixed with 143.3 mg (1 mmol) of copper(I) bromide. 9.4 ml of a 10% solution of trimethyl aluminum in toluene is added over 10 minutes to the reaction under nitrogen atmosphere so that the temperature does not rise above 30° C. Then it is stirred for 2 hours more at 30° C. For hydrolysis, 0.54 ml of water dissolved in 5 ml of dioxane is added to the reaction and stirred for 10 minutes more. The solid is suctioned off on diatomaceous earth and washed again with 20 ml of dioxane. The filtrate is concentrated by evaporation and the crude product (3.5 g) is chromatographed on silica gel with hexane/ethyl acetate mixtures as eluent. After concentration by evaporation of the fractions and recrystallization from acetone, 3.1 g of 17β-acetoxy-1α-methyl-androstan-3-one (89% of theory) of a melting point of 180° C. is obtained.

Variant 2 (in ethyl acetate : 66.1 g (0.2 mol) of 17β-acetoxy-androst-1-en-3-one is dissolved in 350 ml of dry ethyl acetate and mixed with 1.43 g (10 mmol) of copper(I) bromide. 188 ml (0.22 mol) of a 10% solution of trimethyl aluminum in toluene is added over 15 minutes to the reaction under nitrogen atmosphere, so that the temperature does not rise above 25° C. Then it is stirred for 30 minutes more. For hydrolysis, 15 ml of water is added to the reaction and stirred for 40 minutes more. The solid is suctioned off and absorptively precipitated three times, each with 200 ml of dioxane. After concentration by evaporation of the combined organic phases, 65.6 g of 17β-acetoxy-1α-methyl-androstan-3-one (95% of theory) of a melting point of 181° C. is obtained.

EXAMPLE 7

16α-Methyl-pregna-1,4-dien-20-one 3.1 g (10 mmol) of pregna-1,4,16-trien-20-one is mixed in 25 ml of dioxane with 143.4 mg of CuBr. 9.4 ml (11 mmol) of a 10% solution of trimethyl aluminum in toluene is added to the reaction under nitrogen and stirred for 30 minutes at 20–30° C. For hydrolysis, 0.54 ml of water dissolved in 5 ml of dioxane is added to the reaction. It is stirred for 10 minutes more and the precipitate is filtered off. The precipitate is washed again with a little dioxane. The dioxane solution is concentrated by evaporation on a rotary evaporator and the residue is chromatographed on silica gel with ethyl acetate/hexane as eluent. After concentration by evaporation of the fractions, 2.6 g of 16α-methyl-pregna-1,4-dien-20-one (80% of theory) of a melting point of 175° C. is obtained.

Examples 1–7 can be performed analogously in other solvents such as THF, dimethoxyethane or ethyl acetate with CuBr or CuCN as well as other copper salts such as, e.g., $CuBr_2$ or bis-(salicyl-aldehydato)-copper or bis-(N-isopropyl-salicylidene-aminato)-copper, whose production is described in J. Chem. Soc., 1964, 276, with trimethyl aluminum as methylation agent.

EXAMPLE 8

3-Acetoxy-1α-methyl-androsta-2,4-dien-17-one 14.2 g (50 mmol) of androsta-1,4-diene-3,17-dione is dissolved in 100 ml of anhydrous dioxane under nitrogen atmosphere. 716 mg (5 mmol) of copper(I) bromide is added and the solution is heated to 25° C. Then 47 ml (55 mmol) of a 10% solution of trimethyl aluminum in toluene is added to the reaction so that the temperature does not rise above 35° C. Then it is stirred for 1.5 hours more at 35° C. 16.84 g (0.165 mol) of acetic anhydride is added at 35° C. and the reaction solution is stirred for 1 hour more at 30° C. For completion of the reaction it is then heated for 15 minutes to 60° C. After cooling of the solution to 20° C., 4 ml of water dissolved in 20 ml of dioxane is added to the reaction for the hydrolysis and the solution is stirred again for 15 minutes. The inorganic solid is suctioned off on diatomaceous earth and the solid is washed again with 50 ml of dioxane. After concentration by evaporation of the solution on a rotary evaporator, 18 g of crude product is obtained, that is chromatographed on silica gel with hexane and an increasing part of ethyl acetate as eluent. After concentration by evaporation of the fractions, 11.4 g of 3-acetoxy-1α-methyl-androsta-2,4-dien-17-one (70% of theory) is obtained as viscous material that can be recrystallized from diisopropylether.

$^1$H-NMR ($CDCl_3$):δ=0.89 (d, J=7 Hz, 3H,1'-$CH_3$), 0.91 (s, 3H, 19-$CH_3$), 1.05 (s, 3H, 18-$CH_3$), 2.15 (s, 3H, $CH_3CO$-O-), 1.0–2.6 (m, 16H), 5.2–5.4 (m, 2H, H-2, H-4).

EXAMPLE 9

3-Methylcyclohexanone 4.8 g (50 mmol) of cyclohex-2-en-1-one and 716 mg of CuBr are dissolved in 100 ml of absolute tetrahydrofuran under nitrogen atmosphere at 20° C. 47 ml (55 mmol) of a 10% solution of trimethyl aluminum in toluene is added to the reaction at 20° C., so that the temperature does not rise above 20° C. After completion of the addition it is stirred for 30 minutes at 20° C. For hydrolysis, 4 ml of water dissolved in 20 ml of tetrahydrofuran is added and the solution is stirred for 15 minutes at room temperature. The inorganic solid is filtered off and washed again with 50 ml of tetrahydrofuran. After concentration by evaporation of the solution, 5.5 g of crude product is obtained that is distilled at 70° C. and 20 torr. 4.0 g of 3-methylcyclohexanone (71% of theory) is obtained.

EXAMPLE 10

1α-Methyl-androsta-4,6-diene-3,17-dione 2.82 g (10 mmol) of androsta-1,4,6-triene-3,17-dione is dissolved in 20 ml of dioxane at 20° C. and mixed with 143.3 mg (1 mmol) of copper(I) bromide. 9.4 ml (11 mmol) of a 10% solution of trimethyl aluminum in toluene is added to the reaction at room temperature under nitrogen atmosphere and stirred for 10 minutes at 20° C. For hydrolysis, 1 ml of water dissolved in 5 ml of dioxane is carefully added to the reaction. It is stirred for 10 minutes more and the inorganic precipitate filtered off with dioxane is washed again. The dioxane solution is concentrated by evaporation on a rotary evaporator and the residue is chromatographed on silica gel with ethyl acetate/hexane as eluent. After concentration by evaporation of the fractions, 2.97 g of 1α-methyl-androsta-4,6-diene-3,17-dione (99% of theory) of a melting point of 171° C. is obtained.

EXAMPLE 11

3-Acetoxy-16α-methyl-pregn-5-en-20-one (16α-methyl-pregn-5-enolone-3-acetate)

3.56 g (10 mmol) of 3-acetoxy-pregna-5,16-dien-20-one is dissolved in 20 ml of dioxane at 20° C. and mixed with 143.3 g (1 mmol) of copper(I) bromide. 9.4 ml (11 mmol) of a 10% solution of trimethyl aluminum in toluene is added to the reaction at room temperature under nitrogen atmosphere and, after completion of the addition, stirred for 10 minutes at 20° C. For hydrolysis of the reaction solution, 1 ml of water dissolved in 5 ml of dioxane is carefully added to the reaction. It is stirred for 10 minutes more and the inorganic precipitate filtered off with dioxane is washed again. The dioxane solution is concentrated by evaporation on a rotary evaporator and the residue is chromatographed on silica gel with ethyl acetate/hexane as eluent. After concentration by evaporation of the fractions, 1.12 g of 3-acetoxy-16α-methyl-pregn-5-en-20-one (30% of theory) is obtained.

EXAMPLE 12

1α-Ethylandrost-4-ene-3,17-dione 2.84 g (10 mmol) of androsta-1,4-diene-3,17-dione is dissolved in 20 ml of anhydrous dioxane under nitrogen atmosphere. 143 mg (1 mmol) of copper(I) bromide is added and the solution is heated to 25° C. Then 10 ml (10 mmol) of a 1 molar solution of triethyl aluminum in hexane is added to the reaction so that the temperature does not rise above 30° C. Then it is stirred for 1.5 hours more at 30° C. For hydrolysis, 1 ml of water mixed with 5 ml of dioxane is added to the reaction and the solution is stirred for 15 minutes more. The inorganic solid is suctioned off and washed again with 30 ml of dioxane. After concentration by evaporation of the dioxane solution, 3 g of crude product is obtained, that is chromatographed on silica gel with an hexane/ethyl acetate mixture with an increasing part of ethyl acetate as eluent. After concentration by evaporation of the fractions, 2.67 g of 1α-ethylandrost-4-ene-3,17-dione (85% of theory) of a melting point of 168° C. is obtained.

EXAMPLE 13

1α-Ethyl-androsta-4,6-diene-3,17-dione 2.82 g (10 mmol) of androsta-1,4,6-triene-3,17-dione is dissolved in 20 ml of dioxane at 20° C. and mixed with 143.3 g (1 mmol) of copper(I) bromide. 11 ml (11 mmol) of a 1 molar solution of triethyl aluminum in hexane is added to the reaction at room temperature under nitrogen atmosphere and stirred for 2 hours at 30° C. For hydrolysis, 1 ml of water dissolved in 5 ml of dioxane is carefully added to the reaction. It is stirred for 10 minutes more and the inorganic precipitate filtered off with dioxane is washed again. The dioxane solution is concentrated by evaporation on a rotary evaporator and the residue is chromatographed on silica gel with ethyl acetate/hexane as eluent. After concentration by evaporation of the fractions, 1.93 g of 1α-ethyl-androsta-4,6-diene-3,17-dione (62% of theory) of a melting point of 137.1° C. is obtained.

EXAMPLE 14

3-Acetoxy-16α-ethyl-pregn-5-en-20-one (16α-ethyl-pregn-5-enolone-3-acetate)

3.56 g (10 mmol) of 3-acetoxy-pregna-5,16-dien-20-one is dissolved in 20 ml of dioxane at 20° C. and mixed with 143.3 g (1 mmol) of copper(I) bromide. 11 ml (11 mmol) of a 1 molar solution of trimethyl aluminum in hexane is added to the reaction at room temperature under nitrogen atmosphere and, after completion of the addition, stirred for 3 hours more at 22° C. For hydrolysis of the reaction solution, 1 ml of water dissolved in 5 ml of dioxane is carefully added to the reaction. It is stirred for 10 minutes more and the inorganic precipitate is filtered off with dioxane and washed again. The dioxane solution is concentrated by evaporation on a rotary evaporator and the residue is chromatographed on silica gel with ethyl acetate/hexane as eluent. After concentration by evaporation of the fractions, 1.72 g of 3-acetoxy-16α-ethyl-pregn-5-en-20-one (45% of theory) of a melting point of 114.9° C. is obtained.

EXAMPLE 15

4-Phenyl-pentan-2-one 143 mg of CuBr is added to 1.46 g (10 mmol) of cis/trans-benzylideneacetone (3-phenyl-but-3-en-2-one) in 20 ml of absolute dioxane. 9.4 ml (11 mmol) of a 10% solution of trimethyl aluminum in toluene is added to the reaction at room temperature under nitrogen atmosphere and, after completion of the addition, stirred for 10 minutes at 22° C. For hydrolysis of the reaction solution, 1 ml of water dissolved in 5 ml of dioxane is carefully added to the reaction. It is stirred for 10 minutes more and the inorganic precipitate filtered off with dioxane is washed again. The dioxane solution is concentrated by evaporation on a rotary evaporator and the residue is chromatographed on silica gel with ethyl acetate/hexane as eluent. After concentration by evaporation of the fractions, 1.21 g of 4-phenyl-pentan-2-one (75% of theory) is obtained a colorless liquid.

EXAMPLE 16

4-Phenyl-hexan-2-one 143 mg of CuBr is added to 1.46 g (10 mmol) of cis/trans-benzylideneacetone (3-phenyl-but-3-en-2-one) in 20 ml of absolute dioxane. 11 ml (11 mmol) of a 1 molar solution of trimethyl aluminum in hexane is added to the reaction at room temperature under nitrogen atmosphere and, after completion of the addition, stirred for 10 minutes at 22° C. For hydrolysis of the reaction solution, 1 ml of water dissolved in 5 ml of dioxane is carefully added to the reaction. It is stirred for 10 minutes more and the inorganic precipitate filtered off with dioxane is washed again. The dioxane solution is concentrated by evaporation on a rotary evaporator and the residue is chromatographed on silica gel with ethyl acetate/hexane as eluent. After concentration by evaporation of the fractions, 1.37 g of 4-phenyl-hexan-2-one (78% of theory) is obtained a colorless liquid.

EXAMPLE 17

1α-Methylandrost-4-ene-3,17-dione

Addition to androsta-1,4-diene-3,17-dione with $CuBr_2$ with addition of nickel-bis-acetylacetonate [$Ni(AcAc)_2$]: In Aust. J. Chem., 1975, 28, 817 a 1,4-addition only with [$Ni(AcAc)_2$] is described. The reactions described there refer to 3-keto-$\Delta^4$-steroids, the yields achieved there are 30–40% of theory. By $CuBr_2$ addition the reaction occurs with higher yield and better selectivity than with $Ni(AcAc)_2$ catalysis.

2.84 g (10 mmol) of androsta-1,4-diene-3,17-dione is dissolved in 10 ml of anhydrous tetrahydrofuran under nitrogen atmosphere. 223 mg (1 mmol) of copper(II) bromide ($CuBr_2$) and 28.4 mg of $Ni(AcAc)_2$ are added and the solution is cooled to −20° C. 8.5 ml (10 mmol) of a 10% solution of trimethyl aluminum in toluene is added to the reaction at −20° C. and stirred for 30 minutes more with heating to 0° C. For hydrolysis, 1 ml of water dissolved in 2 ml of tetrahydrofuran is added to the reaction and the solution is stirred for 15 minutes more. The inorganic solid is suctioned off and washed again with 30 ml of dioxane. After concentration by evaporation of the solution, 3.2 g of crude product is obtained that is chromatographed on silica gel with hexane/ethyl acetate mixtures as eluent. After concentration by evaporation of the fractions, 2.2 g of 1α-methylandrost-4-ene-3,17-dione (74% of theory) of a melting point of 154° C. as well as 0.55 g of 5β-methylandrost-1-ene-3,17-dione (18.5% of theory) are obtained.

Tests concerning the reaction of α,β-unsaturated ketones with copper(II)-bis-acetylacetonate and trimethyl aluminum

EXAMPLE 18

Test concerning the formation of 1α-methylandrost-4-ene-3,17-dione 2.84 g (10 mmol) of androsta-1,4-diene-3,17-dione is dissolved in 10 ml of anhydrous dioxane under nitrogen atmosphere. 260 mg (1 mmol) of copper(II)-bis-acetylacetonate is added. Then 47 ml (55 mmol) of a 10% solution of trimethyl aluminum in toluene is added to the reaction so that the temperature does not rise above 35° C. Then it is stirred for 6 hours more at 35° C. The reaction was tracked hourly with DC (silica gel-HPTLC, ethyl acetate/hexane 1:1 as eluent). No formation of 1α-methylandrost-4-ene-3,17-dione was detectable, only in addition to unreacted initial material of 30%, 3-exomethylene-androsta-1,4-dien-17-one had developed.

EXAMPLE 19

Test reaction of 3,5,5-trimethylcyclohex-2-en-1-one (isophorone) to 3,3,5,5-tetramethylcyclohexan-1-one with copper(II)-bis-acetylacetonate and trimethyl aluminum according to E. C. Ashby et al.; J. Org. Chem., 1974, 39, 3297

1.38 g of 3,5,5-trimethylcyclohex-2-en-1-one (isophorone) dissolved in 10 ml of ether is mixed with 0.3 mmol $Cu(AcAc)_2$. 9.35 ml of a 10% solution of trimethyl aluminum in toluene is added at 22° C. After 2 hours at 22° C., a check of the reaction for conversion takes place. The reaction is hydrolyzed, extracted with ether and the product is studied with NMR. Only initial material (3,5,5-trimethylcyclohex-2-en-1-one) was recovered, a reaction with copper(II)-bis-acetylacetonate as catalyst was not feasible as examples 18 and 19 showed.

EXAMPLE 20

Production of 1-methyl-androsta-1,2-diene-3,17-dione (atamestan) according to German Patent Application P 4015247.2 a) 2β-Iodo-1α-methylandrost-4-ene-3,17-dione 17.1 g (50 mmol) of 2-acetoxy-1α-methyl-androsta-2,4-dien-17-one (example 8) is dissolved in 85 ml of acetone and mixed with 4.92 g (60 mmol) of anhydrous sodium acetate. After cooling to −10° C., 8.12 g (55 mmol) of iodine chloride is added under nitrogen atmosphere. It is stirred for 30 minutes more at −10° C. The reaction solution is added by stirring in 0.5 l of ice water mixed with 2 g of sodium thiosulfate. The solid is suctioned off and washed again with water. After drying of the substance, 20 g of product (94% of theory) of a melting point of 119° C. (decomp.) is obtained.

b) 1-Methylandrosta-1,4-diene-3,17-dione (atamestan)

2.13 g (5 mmol) of 2β-iodo-1α-methylandrost-4-ene-3, 17-dione from a) is introduced to a suspension, preheated to 130° C., of 0.73 g (10 mmol) of lithium carbonate in 10 ml of dimethylformamide and stirred at this temperature for 1.5 hours. After cooling, the reaction solution is added to 30 ml of water, extracted with ethyl acetate and after drying on sodium sulfate is concentrated by evaporation. The crude product is chromatographed on silica gel with ethyl acetate/hexane as mobile solvent. After recrystallization from ethyl acetate, 1.1 g of 1-methylandrosta-1,4-diene-3,17-dione (74% of theory) of a melting point of 169° C. is obtained.

EXAMPLE 21

17β-Acetoxy-2α-bromo-1α-methyl-5α-androstan-3-one 14.3 mg (0.1 mmol) of CuBr is added at room temperature to 818 mg (2 mmol) of 17β-acetoxy-2-bromo-5α-androst-1-en-3-one (produced according to J. Org. Chem. 1982, 47, 5090; from 17β-acetoxy-2-brom-5α-androst-1-en-3-one) in 4 ml of ethyl acetate. 1.9 ml (2.2 mmol) of a 10% solution of trimethyl aluminum in toluene is instilled at room temperature. It is stirred at room temperature for 45 minutes. For hydrolysis, 0.18 ml of water is added, the solid is suctioned off and washed again with ethyl acetate. The solution is concentrated by evaporation and the residue is chromatographed on silica gel with hexane/ethyl acetate as eluent. After concentration by evaporation of the chromatography fractions, 600 mg of 17β-acetoxy-2α-bromo-1α-methyl-5α-androstan-3-one is obtained.

EXAMPLE 22

17-Acetoxy-1α-ethyl-5α-androstan-3-one 5.78 ml (11 mmol) of a 1.9 molar solution of triethyl aluminum in toluene is added at room temperature to 3.3 g (10 mmol) of 17-acetoxy-5α-androst-1-en-3-one in 15 ml of ethyl acetate and 44.78 mg (0.5 mmol) of copper cyanide (CuCN). It is stirred 12 hours more at 25° C. The reaction solution is hydrolyzed with 1 ml of water and stirred again for 15 minutes. The inorganic solid is filtered off. The solid is washed again with ethyl acetate. After evaporation of the solvent and chromatography of the substance on silica gel with hexane/ethyl acetate as eluent, 1.44 g (39% of theory) of 17-acetoxy-1α-ethyl-5α-androstan-3-one is obtained.

EXAMPLE 23

1-Methyl-7,7-(2,2-dimethyltrimethylene-dioxy)-cis-bicyclo [3.3.0] octan-3-one 1.9 ml (2.2 mmol) of trimethyl aluminum as 10% solution in toluene is added to 444.6 (2 mmol) of 7,7-(2,2-dimethyltrimethylene-dioxy)-cis-bicyclo [3.3.0] oct-1-en-3-one and 28.7 mg (0.2 mmol) of CuBr in 3 ml of dioxane and the solution is stirred at room temperature. After 15 minutes it is hydrolyzed with water, the product is extracted with ethyl acetate and chromatographed on silica gel with hexane with increasing parts of ethyl acetate as eluent. After concentration by evaporation of the fractions, 290 mg (61% of theory) of 1-methyl-7,7-(2,2-dimethyltrimethylene-dioxy)-cis-bicyclo [3.3.0] octan-3-one is obtained.

EXAMPLE 24

1-Ethyl-7,7-(2,2-dimethyltrimethylene-dioxy)-cis-bicyclo [3.3.0] octan-3-one 1.15 ml (2.2 mmol) of a 1.9 molar solution of triethyl aluminum in toluene is added to 444.57 mg (2 mmol) of 7,7-(2,2-dimethyltrimethylene-dioxy)-cis-bicyclo [3.3.0] oct-1-en-3-one and 17.7 mg (0.1 mmol) of CuBr in 4 ml of absolute ethyl acetate. It is stirred for 2 hours at 25° C. The reaction solution is then hydrolyzed with 20 ml of water. It is stirred for 15 minutes more and the product is extracted with ethyl acetate. After evaporation of the solvent and chromatography of the substance on silica gel with hexane/ethyl acetate as eluent, 0.3 g of 1-ethyl-7,7-(2,2-dimethyltrimethylene-dioxy)-cis-bicyclo [3.3.0] octan-3-one (60% of theory) is obtained.

EXAMPLE 25

2-Tert-butyl-5-methyl-cyclohexanone 28.5 ml (33 mmol) of trimethyl aluminum as 10% solution in toluene is instilled in 4.56 g (30 mmol) of 2-isopropylidene-5-methyl-cyclohexan-1-one (pulegon) and 214.5 mg (1.5 mmol) of CuBr in 30 ml of ethyl acetate. The reaction solution is stirred 1 hour more at 25° C. 2 ml of water is carefully added for hydrolysis and stirred for 15 minutes more. The inorganic solid is suctioned off, washed again with ethyl acetate and the solution is concentrated by evaporation in a vacuum. Distillation of the crude product at 120° C./6 torr yields 3.4 g of 2-tert-butyl-5-methyl-cyclohexanone (70% of theory) as isomer mixture.

EXAMPLE 26

3,3,5,5-Tetramethylcyclohexanone 1.38 g of 3,5,5-tetramethylcyclohex-2-en-1-one (isophorone) is dissolved in 10 ml of dioxane and 143 mg (1 mmol) of CuBr is added. 9.4 ml (11 mmol) of trimethyl aluminum 10% in toluene is added at room temperature. The solution is stirred for 1 hour at room temperature. For hydrolysis, 1 ml of water is added, the solution is diluted with ethyl acetate, the solid is filtered off and washed again with ethyl acetate. After evaporation of the solvent and chromatography of the substance on silica gel with hexane/ethyl acetate as eluent, 1.20 g (78% of theory) of 3,3,5,5-tetramethylcyclohexanone is obtained.

EXAMPLE 27

17β-Acetoxy-1α-methyl-5α-androstan-3-one a) In situ production of dimethyl aluminum-ethoxide 0.506 g (11 mmol) of absolute ethanol is added to 11 mmol (9.5 mmol) of a 10% solution of trimethyl aluminum in toluene at 0° C. It is stirred for 10 minutes more.

b) Reaction of 17β-acetoxy-1α-methyl-5α-androstan-3-one 3.3 g (10 mmol) of 17β-acetoxy-5α-androst-1-en-3-one in 15 ml of ethyl acetate and 143 mg (0.1 mmol) of CuBr are added to solution a). It is stirred for 16 hours at 25° C. The reaction solution is hydrolyzed with 1 ml of water, stirred for 15 minutes more and the inorganic solid is filtered off. The solid is washed with ethyl acetate. After evaporation of the solvent, 3.5 g of substance is obtained that is recrystallized from acetone. After suctioning off of the crystals, 2.9 g of 17-acetoxy-1α-methyl-5α-androstan-3-one of a melting point of 179-180° C. is obtained.

We claim:

1. A combination of a compound to be alkylated and a methylation or ethlylation agent comprising a compound selected fron the group consisting of trimethyl aluminum, dimethyl zinc and triethyl aluminum as a source of methyl or ethyl, and 1–10 mole % per mole of compound to be alkylated of one or more copper compounds selected from the group consisting of: a) copper (I) compounds of formula I; b) copper (II) compounds of formula I, $$CuX \text{ or } CuX_2 \tag{I}$$

wherein X is a monovalent radical and stands for chlorine, bromine, iodine, cyano, thienyl, phenyl, alkoxy of 1 to 8 carbon atoms optionally branched and/or unsaturated, thio-alkoxy wherein the alkyl radical has 1–8 carbon atoms and is optionally branched and/or unsaturated, a substituted alkinyl radical R—C≡C— (wherein R is phenyl or an optionally branched $C_1$–$C_8$-alkyl radical), an inorganic acid radical, a carboxylic acid, or a bidentate complex ligand coordinated by oxygen atoms, nitrogen atoms or both, excluding the ligand acetylacetonate in the case of the divalent coppers; c) compounds of formula II $$Cu_2Y \text{ or } CuY \tag{II}$$

wherein Y is a divalent radical and stands for oxygen or sulfur; and d) combination thereof.

2. A methylation or ethylation agent according to claim 1, wherein said agent is copper (I)-chloride, copper (I)-bromide, copper (I)-cyanide, copper (II)-chloride copper (II)-bromide or combinations thereof.

3. A combination of a compound to be alkylated and a methylation or ethylation agent comprising an aluminum reagent $Alk_{3-n}AlOEt_n$ as a source of methyl or ethyl, wherein Alk is methyl or ethyl, OEt is ethoxy, and n is 1 or 2, and 1–10 mole % per mole of compound to be alkylated of one or more copper compound selected from the group consisting of: a) copper (I) compounds of formula I; b) copper (II) compounds of formula I, $$CuX \text{ or } CuX_2 \tag{I}$$

wherein X is a monovalent radical and stands for chlorine, bromine, iodine, cyano, thienyl, phenyl, alkoxy of 1 to 8 carbon atoms optionally branched and/or unsaturated, thioalkoxy wherein the alkyl radical has 1–8 carbon atoms and is optionally branched and/or unsaturated, a substituted alkinyl radical R—C≡C— (wherein R is phenyl or an optionally branched $C_1$–$C_8$-alkyl radical), an inorganic acid radical, a carboxylic acid, or a bidentate complex ligand coordinated by oxygen atoms, nitrogen atoms or both, excluding the ligand acetylacetonate in the case of the divalent coppers; c) compounds of formula II $$Cu_2Y \text{ or } CuY \qquad (II)$$

wherein Y is a divalent radical and stands for oxygen or sulfur; and d) combinations thereof.

4. A methylation or ethylation agent comprising a compound selected from the group consisting of trimethyl aluminum, dimethyl zinc and triethyl aluminum as a source of methyl or ethyl, and one or more copper compounds selected for the group consisting of: a) copper (I) compounds of formula I; b) copper (II) compounds of formula I $$CuX \text{ or } CuX_2 \qquad (I)$$

wherein X is a monovalent radical and stands for chlorine, bromine, iodine, cyano, thienyl, phenyl, alkoxy of 1 to 8 carbon atoms optionally branched and/or unsaturated, thioalkoxy wherein the alkyl radical has 1–8 carbon atoms and is optionally branched and/or unsaturated, a substituted alkinyl radical R—C≡C— (wherein R is phenyl or an optionally branched $C_1$–$C_8$-alkyl radical), an inorganic acid radical, a carboxylic acid, or a bidentate complex ligand coordinated by oxygen atoms, nitrogen atoms or both, excluding the ligand acetylacetonate in the case of the divalent coppers; c) compounds of formula II $$Cu_2Y \text{ or } CuY \qquad (II)$$

wherein Y is a divalent radical and stands for oxygen or sulfur; and d) combinations thereof,
wherein said agent additionally contains up to 1 mol % of nickel salt(s).

5. A methylation or ethylation agent according to claim 4 wherein said nickel salt is nickel-II-acetylacetonate, nickel-bis-triphenylphos-phane-dichloride or nickel dichloride.

6. A process for 1–4-addition of a methyl or ethyl group of an α,β-unsaturated, an α,β-double unsaturated ketone or an α,β-unsaturated aldehyde, comprising alkylating said α,β-unsaturated ketone, α,β-double unsaturated ketone or the α,β-unsaturated aldehyde with a methylation of ethylation agent comprising a compound selected from the group consisting of aluminum trimethyl, zinc dimethyl and aluminum triethyl in the presence of a catalytic amount of one or more copper compounds selected from the group consisting of: a) copper (I) compounds of formula I; b) copper (II) compounds or formula I, $$CuX \text{ or } CuX_2 \qquad (I)$$

wherein X is a monovalent radical and stands for chlorine, bromine, iodine, cyano, thienyl, phenyl, an alkoxy of 1 to 8 carbon atoms optionally branched and/or unsaturated, thioalkoxy wherein the alkyl radical has 1–8 carbon atoms and is optionally branched and/or unsaturated, a substituted alkinyl radical R—C≡C— (wherein R is phenyl or an optionally branched $C_1$–$C_6$-alkyl radical), an inorganic acid radical, a carboxylic acid, or a bidentate complex ligand coordinated by oxygen atoms, nitrogen atoms or both, excluding the ligand acetylacetonate in the case of the divalent coppers; c) compounds of formula II $$Cu_2Y \text{ or } CuY \qquad (III)$$

wherein Y is a divalent radical and stands for oxygen or sulfur; and d) combinations thereof.

7. A process according to claim 6, wherein alkylation is carried out in the presence of 1–10 mol % per mole of α,β-unsaturated ketone to be alkylated, of copper compounds selected from the group consisting of copper (I) compounds and copper (II) compounds, wherein the yield of addition product is above 70% of theory.

8. A process according to claim 6, wherein alkylation is carried out in the presence of copper (I) chloride, copper (I) bromide, copper (II)-chloride copper (II) bromide, copper (I)-cyanide or a combination thereof and wherein the yield of addition product is above 70% of theory.

9. A process according to claim 6, wherein up to 1 mol % of nickel salt is present.

10. A process according to claim 9, wherein said nickel salt is nickel-II-acetylacetonate, nickel-bis-triphenylphosphane-dichloride or nickel dichloride.

11. A process according to claim 6, wherein alkylation is performed at a temperature of 0° C.–50° C.

12. A process according to claim 6, wherein said α,β-unsaturated ketone is a 3-keto-1,4-diene steroid, a 3-keto-1-ene steroid, a 3-keto-4-ene steroid or a 17-acyl-16-ene steroid.

13. A process for production of 1α-methylandrost-4-ene-3,17-dione, comprising methylating androsta-1,4-diene-3,17-dione according to the process of claim 6.

14. A process according to one of preceding claim 7, wherein alkylation is performed in ethyl acetate, tetrahydrofuran, dioxane, dimethoxyethane or toluene as solvent.

15. A process for 1,4-addition of a methyl or ethyl group to an α,β-unsaturated, an α,β-double unsaturated ketone or an α,β-unsaturated aldehyde, comprising alkylating said α,β-unsaturated ketone, α,β-double unsaturated ketone, or α,β-unsaturated aldehyde in the presence of a catalytic amount of a methylation or ethylation agent comprising an aluminum reagent $Alk_{3-n}AlOEt_n$ as a source of methyl or ethyl, wherein Alk is methyl or ethyl, OEt is ethoxy, and n is 1 or 2, and a catalytic amount of one or more copper compounds selected from the group consisting of: a) copper (I) compounds of formula (I); b) copper (II) compounds of formula I $$CuX \text{ or } CuX_2 \qquad (I)$$

wherein X is a monovalent radical and stands for chlorine, bromine, iodine, cyano, thienyl, phenyl, alkoxy of 1 to 8 carbon atoms optionally branched and/or unsaturated, thioalkoxy wherein the alkyl radical has 1–8 carbon atoms and is optionally branched and/or unsaturated, a substituted alkinyl radical R—C≡C— (wherein R is phenyl or an optionally branched $C_1$–$C_8$-alkyl radical), an inorganic acid radical, a carboxylic acid, or a bidentate complex ligand coordinated by oxygen atoms, nitrogen atoms or both, excluding the ligand acetylacetonate in the case of the divalent coppers; c) compounds of formula II $$Cu_2Y \text{ or } CuY \qquad (II)$$

wherein Y is a divalent radical and stands for oxygen or sulfur; and d) combination thereof.

16. A process according to claim 15, wherein alkylation is carried out in the presence of 1–10 mol % of one or more copper compounds selected from the group consisting of copper (I) b) compounds and copper (II) compounds, relative to said α, β-unsaturated ketone to be alkylated.

17. A process for production of 1α-methylandrost-4-ene-3,17-dione, comprising methylating androsta-1,4-diene-3,17-dione according to the process of claim 15.

18. A process for production of a 3-acyloxy-1α-methyl-androsta-2,4-dien-17-one, comprising methylating androsta-1,4-diene-3,17-dione according to the process of claim 15, and, trapping after the methylation the enolate present in the reaction mixture with a carboxylic acid anhydride or chloride of a straight or branched chain alkane carboxylic acid with 2–8 carbon atoms or benzoic acid.

19. A process for production of a 3-acyloxy-1α-methyl-androsta-2,4-dien-17-one, comprising the step of methylating androsta-1,4-diene-3,17-dione to from an intermediate wherein methlylation is achieved with a compound selected from the group consisting of aluminum trimethyl, zinc dimethyl and aluminum triethyl in the presence of a catalytic amount of one or more copper compounds selected from the group consisting of: a) copper (I) compounds of formula I; b) copper (II) compounds of formula I $$CuX \text{ or } CuX_2 \quad (I)$$

wherein X is a monovalent radical and stands for chlorine, bromine, iodine, cyano, thienyl, phenyl, an alkoxy of 1 to 8 carbon atoms optionally branched and/or unsaturated, thio-alkoxy wherein the alkyl radical has 1–8 carbon atoms and is optionally branched and/or unsaturated, a substituted alkinyl radical R—C≡C— (wherein R is phenyl or an optionally branched $C_1$–$C_8$-alkyl radical), an inorganic acid radical, a carboxylic acid, or a bidentate complex ligand coordinated by oxygen atoms, nitrogen atoms, or both excluding the ligand acetylacetonate in the case of the divalent coppers; c) compounds of formula II $$Cu_2Y \text{ or } CuY \quad (II)$$

wherein Y is a divalent radical and stands for oxygen or sulfur; and d) combinations thereof, and trapping after the methylation, the enolate present in the reaction mixture with a carboxylic acid anhydride or chloride of a straight or branched chain alkane carboxylic acid with 2–8 carbon atoms or benzoic acid.

20. A process according to claim 19, wherein the enolate is trapped with acetanhydride or acetyl chloride.

21. A process for 1,4-addition of a methyl or ethyl group to an α,β-unsaturated an α,β-double unsaturated ketone or an α,β-unsaturated aldehyde, comprising alkylating said α,β-unsaturated ketone, α,β-double unsaturated ketone, or α,β-unsaturated aldehyde with a methylation or ethylation agent comprising a compound selected from the group consisting of:

trimethyl aluminum, dimethyl zinc and triethyl aluminum as a source of methyl or ethyl, and one or more compounds selected from the group consisting of: a) copper (I) compounds of formula I; b) copper (II) compounds of formula I $$CuX \text{ or } CuX_2 \quad (I)$$

wherein X is a monovalent radical and stands for chlorine, bromine, iodine, cyano, thienyl, phenyl, alkoxy of 1 to 8 carbon atoms optionally branched and/or unsaturated, thio-alkoxy wherein the alkyl radical has 1–8 carbon atoms and is optionally branched and/or unsaturated, a substituted alkinyl radical R—C≡C— (wherein R is phenyl or an optionally branched $C_1$–$C_8$-alkyl radical), an inorganic acid radical, a carboxylic acid, or a bidentate complex ligand coordinated by oxygen and/or nitrogen atoms, excluding the ligand acetylacetonate in the case of the divalent coppers; c) compounds of formula II $$Cu_2Y \text{ or } CuY \quad (II)$$

wherein Y is a divalent radical and stands for oxygen or sulfur d) combinations thereof wherein alkylation is performed with a combination of compounds of formula I and compounds of formula II.

* * * * *